United States Patent
He et al.

(10) Patent No.: US 10,925,498 B2
(45) Date of Patent: *Feb. 23, 2021

(54) AMBIENT LIGHT FILTER AND ASSOCIATED PHOTO SENSOR HAVING A FIRST DETECTION MODE IN AT LEAST ONE OPTICAL PULSE GAP

(71) Applicant: Silergy Semiconductor Technology (Hangzhou) LTD, Hangzhou (CN)

(72) Inventors: Huisen He, Hangzhou (CN); Baoyu Zhang, Hangzhou (CN); Yanni Zhang, Hangzhou (CN); Lili Shao, Hangzhou (CN)

(73) Assignee: Silergy Semiconductor Technology (Hangzhou) LTD, Hangzhou (CN)

( * ) Notice: Subject to any disclaimer, the term of this patent is extended or adjusted under 35 U.S.C. 154(b) by 999 days.

This patent is subject to a terminal disclaimer.

(21) Appl. No.: 15/477,036

(22) Filed: Apr. 1, 2017

(65) Prior Publication Data
US 2017/0303803 A1    Oct. 26, 2017

(30) Foreign Application Priority Data

Apr. 21, 2016    (CN) .......................... 201610255885.9

(51) Int. Cl.
*A61B 5/1455*    (2006.01)
*A61B 5/024*    (2006.01)
(Continued)

(52) U.S. Cl.
CPC ...... *A61B 5/02427* (2013.01); *A61B 5/14552* (2013.01); *A61B 5/6887* (2013.01);
(Continued)

(58) Field of Classification Search
CPC .............. A61B 5/02427; A61B 5/0044; A61B 5/14552; A61B 5/6826; A61B 5/02416;
(Continued)

(56) References Cited

U.S. PATENT DOCUMENTS 4,258,719 A * 3/1981 Lewyn ............... A61B 5/02416
                                                    307/650
6,987,258 B2    1/2006 Mates
(Continued)

OTHER PUBLICATIONS

Lingfeng Shi, Design of an Infrared Proximity Sensor with Environment Noise Suppression, Huazhong University of Science and Technology (Natural Science Edition), Feb. 2012, pp. 71-76, vol. 40, No. 2, China.

*Primary Examiner* — Que Tan Le
(74) *Attorney, Agent, or Firm* — Michael C. Stephens, Jr.

(57) ABSTRACT

An ambient light filter configured to filter ambient light noises from an optical current that is at least partially caused by an optical pulse sequence emitted by a light emitting device, can include: a sample and detection circuit configured to sample the optical current and to obtain a current component in a first mode, and to remove the current component from the optical current and to generate a detection signal in a second mode; a current amplifier configured to receive the detection signal, and to generate an amplified current signal; and a control circuit configured to switch the sample and detection circuit between the first and second modes, where the control circuit switches the sample and detection circuit to the first mode in at least one optical pulse gap, and switches the sample and detection circuit to the second mode when a next optical pulse arrives.

12 Claims, 4 Drawing Sheets

(51) Int. Cl.
- *A61B 5/00* (2006.01)
- *G01K 11/32* (2021.01)
- *H04B 10/116* (2013.01)
- *H04B 10/80* (2013.01)
- *G06K 9/00* (2006.01)

(52) U.S. Cl.
CPC .......... *A61B 5/7203* (2013.01); *A61B 5/7225* (2013.01); *G01K 11/32* (2013.01); *H04B 10/116* (2013.01); *H04B 10/807* (2013.01); G06K 2009/0006 (2013.01)

(58) Field of Classification Search
CPC . A61B 5/7203; G01J 1/16; G01J 1/44; G06K 2009/006; G01K 11/32; H04B 10/116; H04B 10/807
USPC ........................................ 250/214 AL, 214 R
See application file for complete search history.

(56) References Cited

U.S. PATENT DOCUMENTS

| | | |
|---|---|---|
| 7,244,919 B2 | 7/2007 | Ishikawa et al. |
| 8,097,840 B2 | 1/2012 | Zheng et al. |
| 9,385,667 B2 | 7/2016 | Lichtenegger et al. |
| 10,121,815 B2 * | 11/2018 | Shao ........................ G01J 1/16 |

* cited by examiner

AMBIENT LIGHT FILTER AND ASSOCIATED PHOTO SENSOR HAVING A FIRST DETECTION MODE IN AT LEAST ONE OPTICAL PULSE GAP

RELATED APPLICATIONS

This application claims the benefit of Chinese Patent Application No. 201610255885.9, filed on Apr. 21, 2016, which is incorporated herein by reference in its entirety.

FIELD OF THE INVENTION

The present invention generally relates to the field of sensors, and more particularly to ambient light filters, photo sensors, and associated photo detectors.

BACKGROUND

A photo sensor is a sensor that uses a photo element as a detection element. The photo sensor may initially convert measured changes into optical signal changes, and then convert the optical signal to an electric signal by the photo element. Photo sensors are widely used in heart rate detectors. A heart rate detector can detect a person's heart rate, such that people can determine their own health status based on the detected heart rate. Systole and diastole of the heart causes blood to flow in the blood vessels, and the amount of blood flowing through the blood vessels correspond to different reflectivity. A heart rate detector may calculate the current heart rate by detecting fluctuations of the reflected light.

DETAILED DESCRIPTION

Figure 1:
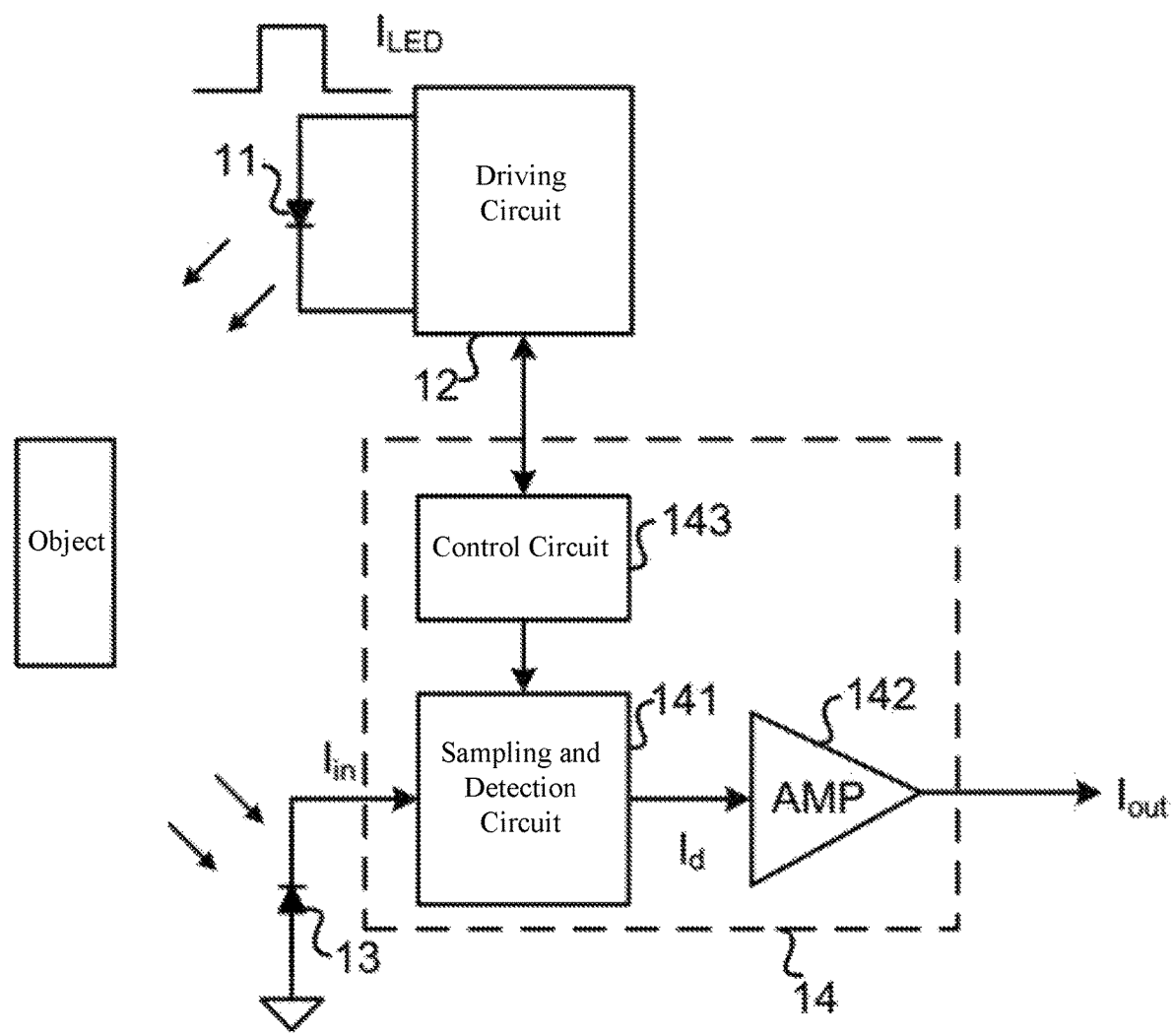
FIG. 1 is a schematic block diagram of an example photo sensor, in accordance with embodiments of the present invention.

Reference may now be made in detail to particular embodiments of the invention, examples of which are illustrated in the accompanying drawings. While the invention may be described in conjunction with the preferred embodiments, it may be understood that they are not intended to limit the invention to these embodiments. On the contrary, the invention is intended to cover alternatives, modifications and equivalents that may be included within the spirit and scope of the invention as defined by the appended claims. Furthermore, in the following detailed description of the present invention, numerous specific details are set forth in order to provide a thorough understanding of the present invention. However, it may be readily apparent to one skilled in the art that the present invention may be practiced without these specific details. In other instances, well-known methods, procedures, processes, components, structures, and circuits have not been described in detail so as not to unnecessarily obscure aspects of the present invention.

A person may be required to place their fingers or wrists close to a chip when a heart rate sensor is used to detect there heart rate. A light emitting device inside the heart rate sensor chip can emit a detection light, and then the photo-electric conversion circuit can detect the intensity of the detection light that is reflected from the finger or wrist. The photo-electric conversion circuit can generate an optical current by way of illumination, and can convert the optical current to a numerical value through an analog-to-digital conversion circuit. In this way, a person's heart rate may be detected by executing a number of continuous detection actions.

However, in in some cases, the photo-electric conversion circuit may only be exposed to the detection light that is reflected back by blood in the fingers or wrist, but can also be exposed to the ambient light (e.g., sunlight, lamplight, etc.). The change of ambient light may seriously affect the detection accuracy of a heart rate detection sensor, and may even cover up small fluctuations of the reflected light due to the blood fluctuations, which can lead to detection failure.

In some approaches, the effect of the ambient light can be overcome by increasing the amplitude of the reflected detection signal by increasing the driving current of the light emitting device. However, power consumption can be increased in such cases, which may be adverse to portable device applications. In addition, the ambient light may be detected for a fixed time period prior to detecting the heart rate, and parameters of the ambient light can be filtered from the detection signal when detecting the heart rate. However, as the ambient light changes in real time, fluctuations of the ambient light may easily cover up the reflected detection signal.

In one embodiment, an ambient light filter configured to filter ambient light noises from an optical current that is at least partially caused by an optical pulse sequence emitted by a light emitting device, can include: (i) a sample and detection circuit configured to sample the optical current and to obtain a current component in a first mode, and to remove the current component from the optical current and to generate a detection signal in a second mode; (ii) a current amplifier configured to receive the detection signal, and to generate an amplified current signal; and (iii) a control circuit configured to switch the sample and detection circuit between the first and second modes, where the control circuit switches the sample and detection circuit to the first mode in at least one optical pulse gap, and switches the sample and detection circuit to the second mode when a next optical pulse arrives.

Referring now to FIG. 1, shown is a schematic block diagram of an example photo sensor, in accordance with embodiments of the present invention. As shown in FIG. 1, photo sensor can include light emitting device 11, driving circuit 12, photo-electric conversion circuit 13, and ambient light filter 14. Light emitting device 11 (e.g., a light emitting diode [LED]) can emit an optical signal, and driving circuit 12 can drive light emitting device 11 to operate according to a driving signal. Photo-electric conversion circuit 13 (e.g., an optical diode fabricated on a semiconductor substrate) can generate an optical current according to an optical signal. Those skilled in the art will recognize that photo-electric conversion circuit 13 may not discriminate between the detection light and the ambient light, but can convert all of the received optical signals into a photo current. During a heart rate detection period, the photo current can at least partially be caused by the light generated by light emitting device 11 and reflected by the object. While not in the detection period, or when light emitting device 11 is not emitting light, the optical current may be caused by the ambient light. For a time period including the detection period, the photo current can at least partially be caused by light generated by light emitting device 11.

Ambient light filter 14 can be coupled to photo-electric conversion circuit 13 through an optical current input terminal. Ambient light filter 14 can sample the ambient light of the photo current, and filter the current component caused by the ambient light, in order to provide a current signal that represents the intensity of the detection light reflected by the object. In this example, driving circuit 12 can drive light emitting device 11 to emit light pulses by continuous pulse signal sequences, i.e., light emitting device 11 may flicker by a predetermined pulse. Thus, the light reflected by the object may flicker along with the light source. Every light reflected by the object may represent the property of the detected object at a corresponding time, such as the position or color property of the object. Thus, in response to the pulse signal sequence, a sequence in which the object property changes over time during the time period can be obtained, in order to complete the detection.

Ambient light filter 14 in this example can be coupled to the driving circuit or the control circuit, in order to obtain the driving signal sequence of the light emitting device. Ambient light filter 14 can start ambient light detection prior to the detection (e.g., before the start of the light pulse sequence) beginning. In addition, ambient light filter 14 can detect the ambient light in the gap of light pulses of the light pulse sequence. Thus, ambient light can be sampled one or more times during the detection, and may be dynamically filtered based on the dynamic variation of the ambient light without increasing the power consumption. In this way, the accuracy of the photo sensor and the associated photo detector can be improved.

In this example, ambient light filter 14 can include sample and detection circuit 141, current amplifier 142 and control circuit 143. Sample and detection circuit 141 can sample the optical current and obtains the current component in a first mode, and may remove the current component from the optical current and output detection signal $I_d$ in a second mode. Current amplifier 142 can generate amplified current signal $I_{out}$ according to detection signal $I_d$ or $V_d$. For example, current amplifier 142 may be an error amplifier, a telescopic cascode amplifier, or a folded cascode amplifier. Control circuit 143 may switch sample and detection circuit 141 between the first and second modes. For example, control circuit 143 can switch sample and detection circuit 141 to the first mode in at least one optical pulse gap, and may switch sample and detection circuit 141 to the second mode when the next optical pulse arrives.

Control circuit 143 may be a separate control circuit, or a common control circuit that is shared by other circuits of the photo detector. In addition, the control circuit can be integrated with other circuitry in an integrated circuit chip, or can be an independent integrated circuit. For example, control circuit 143 can be switched to the first mode in every optical pulse gap. Thus, the ambient light can be detected each time after the emitting device stops emitting light for the entire optical pulse sequence. Also, the ambient light can be detected in a corresponding optical pulse gap every few optical pulses. As such, control circuit 143 may switch sample and detection circuit 14 to the first mode in the optical pulse gap for each of a predetermined number of optical pulse periods.

Figure 2:
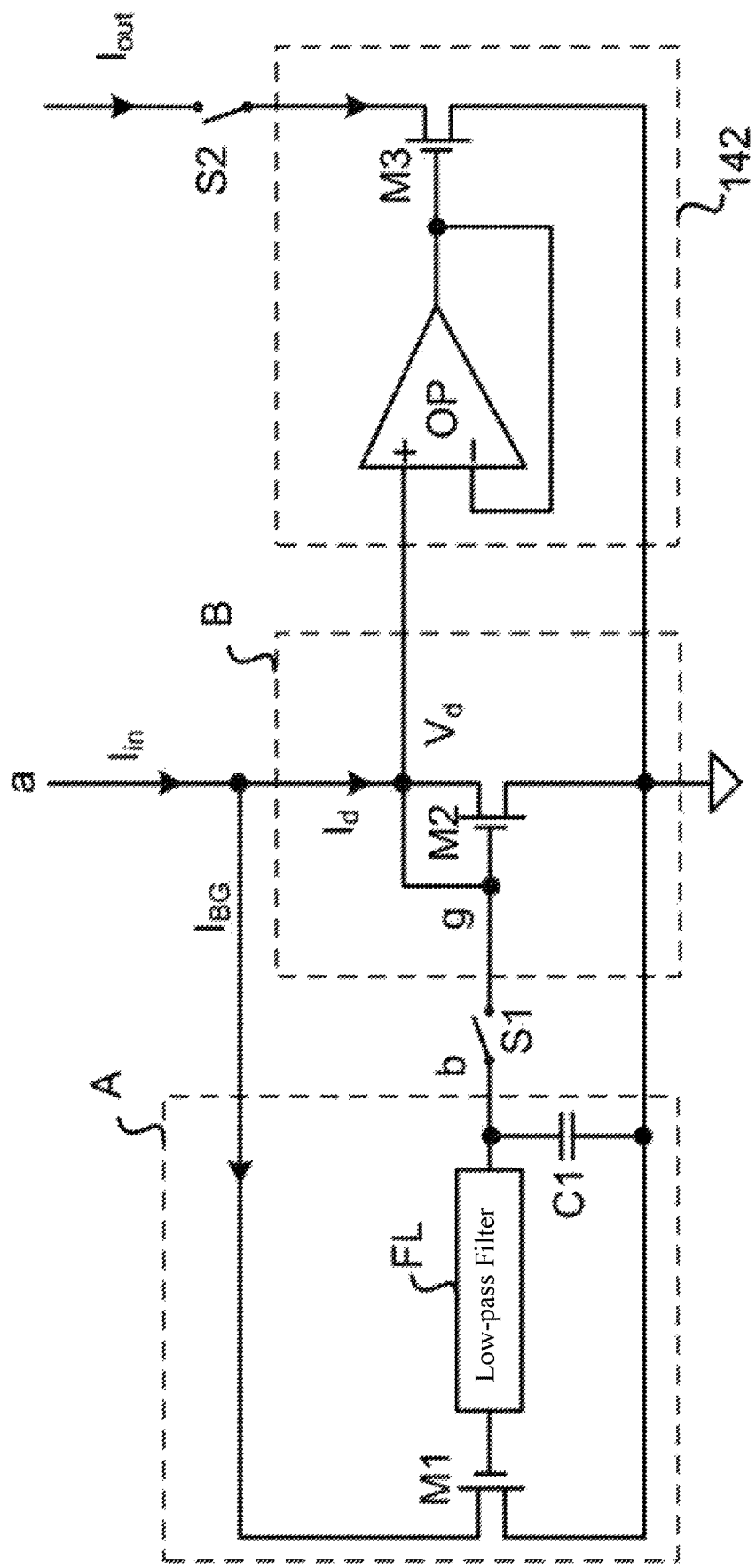
FIG. 2 is a schematic block diagram of a first example ambient light filter, in accordance with embodiments of the present invention.
Figure 3:
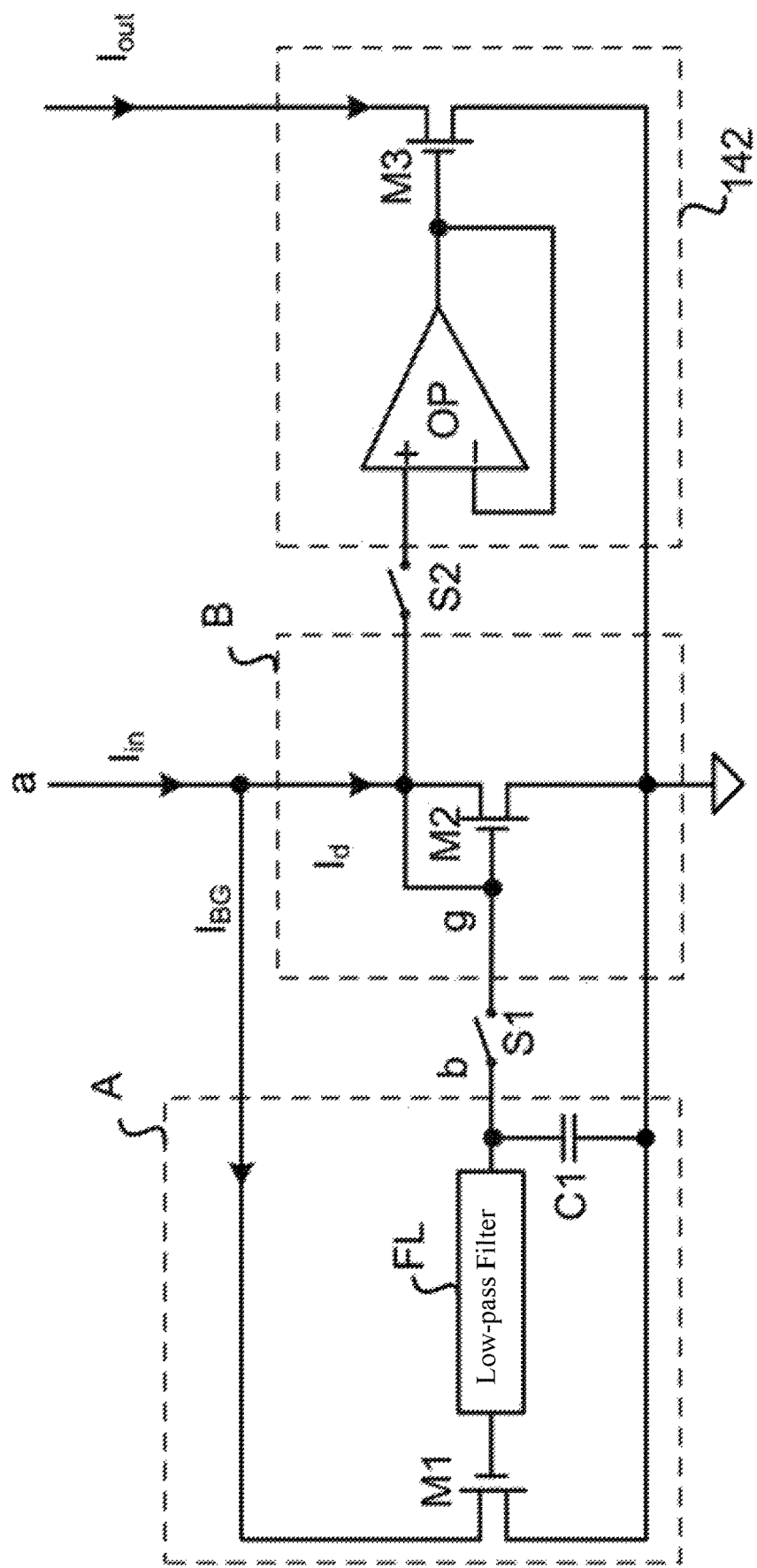
FIG. 3 is a schematic block diagram of a second example ambient light filter, in accordance with embodiments of the present invention.

Referring now to FIGS. 2 and 3, shown are schematic block diagrams of example ambient light filters, in accordance with embodiments of the present invention. Sample and detection circuit 141 can include sample and hold circuit A, current detection circuit B, and switch 51. Sample and hold circuit A can connect to an optical current input terminal "a" that is coupled to the photoelectric conversion circuit in order to receive optical current $I_{in}$. The sample and hold circuit A may cause the optical current of a first proportion to flow in the first mode, and can maintain the current intensity in the second mode.

Current detection circuit B may also be coupled to the optical current input terminal "a," and can form a current mirror together with sample and hold circuit A in the first mode. This arrangement can cause the optical current of a second proportion to flow in the first mode, and may allow the optical current shunted by the sample and hold circuit A to flow in the second mode, in order to output detection signal $I_d$ or $V_d$. For example, the first proportion can be far greater than the second proportion. Thus, the optical current of the first proportion can approximatively represent the optical current caused by the ambient light in the optical pulse gap. For example, the sum of the first and second proportions can be 1, and the first proportion may be set as 2N times the second proportion (e.g., N is greater than or equal to 3, the first proportion is 23 times the second proportion).

Switch S1 can connect between sample and hold circuit A and current detection circuit B, for controlling the mode of sample and hold circuit 141. When switch S1 is turned on, sample and hold circuit A and current detection circuit B may form a current mirror, and operate in the first mode. When switch S1 is turned off, sample and hold circuit A and current detection circuit B are off, sample and hold circuit A can maintain the current, and current detection circuit B can allow the optical current shunted by sample and hold circuit A to flow, so both circuits may operate in the second mode. Control circuit 143 can generate a control signal to switch S1 to control switch S1 to turn on/off, in order to control sample and detection circuit 141 to switch between the first and second modes.

For example, sample and hold circuit A can include transistor M1 (e.g., a field effect transistor [MOSFET]), low-pass filter FL, and capacitor C1. Transistor M1 can connect between the optical current input terminal and ground. As such, the source and the drain of transistor M1 can be respectively connected to the optical current input terminal "a" and ground. Such a relationship may be reversed as desired depending on the type of transistor M1. Low-pass filter FL can connect between the gate of transistor M1 and mode control terminal "b," and capacitor C1 can connect between the mode control terminal and ground.

Current detection circuit B may be configured as a current branch for mirroring the current of sample and hold circuit A, so as to form a current mirror with sample and hold circuit A when switch S1 is turned on. For example, current detection circuit B can include transistor M2 (e.g., a field effect transistor [MOSFET]) that is coupled between optical current input terminal "a" and ground. As such, the gate and drain of transistor M2 may be respectively coupled to the optical current input terminal and ground. Such a relationship may be reversed as desired depending on the type of transistor M2. Also, gate "g" and the source of transistor M2 can be connected together. One terminal of switch S1 can connect to the mode control terminal "b," and the other terminal of switch S1 can connect to the gate of transistor M2.

Thus, when switch S1 is turned on, sample and hold circuit A and current detection circuit B may form a current mirror with their input terminals being coupled to the optical current input terminal. Thus, current flowing through the sample and hold circuit A can be proportional to the current flowing through current detection circuit B based on the principles of the current mirror. As such, the optical current of the first proportion may flow through sample and hold circuit A, and the optical current of the second proportion may flow through current detection circuit B. The flow capacity of a transistor increases as its size increases, so when the size of transistor M1 is set to be far greater than the size of transistor M2, most of the optical current may flow through transistor M1 when switch S1 is turned on.

Alternatively, transistor M1 of a larger size may be replaced by a plurality of transistors M1 with each having the same size as the size of transistor M2. When a plurality of transistors M1 are coupled together (e.g., the sources, the drains, and the gates of transistors M1 are coupled together), the entirety of the plurality of parallel coupled transistors M1 may have far greater flow capacity than transistor M2. When switch S1 is turned off, capacitor C1 can maintain the voltage at mode control terminal "b" as substantially constant, and low-pass filter FL can prevent the variation of the voltage at the gate of transistor M1 that may be caused by noises or abnormal mutation of the ambient light.

Since the gate voltage of transistor M1 may be maintained as constant, the current flowing through transistor M1 can accordingly be maintained as stable. Thus, in the second mode, sample and hold circuit A can maintain the current component corresponding to the sampled ambient light. In addition, when switch S1 is turned off, transistor M2 may remain on to allow the current to flow. The current can be obtained by subtracting current component $I_{BG}$ that is shunted by transistor M1 from current $I_{in}$ at the optical current input terminal. Thus, the current flowing through transistor M2 can precisely represent the optical signal that is obtained by filtering the ambient light from the received light.

It should be understood that sample and hold circuit A and the current detection circuit B shown in FIGS. 2 and 3 are only examples, and those having skilled in the art will recognize that sample and hold circuit A can also be formed by employing a source current branch of a given current mirror circuit (e.g., a cascode current mirror), and current detection circuit B can be formed by employing a mirror current branch of the corresponding current mirror circuit, in order to realize substantially the same function. For example, ambient light filter 14 can also include switch S2 that is coupled to the current amplifier. The current amplifier can be enabled when switch S2 is turned on, and disabled when switch S2 is turned off.

For example, switch S2 can be coupled to the output current path of the current amplifier (as shown in FIG. 2), or coupled to the input current path (as shown in FIG. 3). Correspondingly, control circuit 143 can control switch S2 to turn off when switch S1 is turned on, and may control switch S2 to turn on when switch 51 is turned off. Thus, when switch S1 is turned on, sample and detection circuit 141 can operate in the first mode in order to sample the current component that corresponds to the ambient light, and switch S2 can be turned off to disable current amplifier 142. When switch S1 is turned off, sample and detection circuit 141 may operate in the second mode, in order to generate a detection signal that represents the optical signal obtained by filtering the ambient light from the received light. Also, switch S2 can be turned on to enable current amplifier 142, and the detection signal may be amplified to generate the current signal. In this way, the current signal can continue to be provided after the ambient light has been filtered.

Those having skilled in the art will recognize that switch S2 in the ambient light filter of FIGS. 2 and 3 may not be needed in some cases. For example, if there is no switch S2, the current amplifier may amplify the detection signal of current detection circuit 141 without distinguish the operation modes thereof. In such a case, the signal that represents the intensity of the detection light can be obtained by processing the current outputted by the current amplifier according to the control sequence provided by control circuit 143. The accuracy of current component obtained after filtering the ambient light from the optical current may not be substantially effected regardless of which approach is employed.

As shown in FIGS. 2 and 3, the current amplifier can include operational amplifier OP and transistor M3. The gate of transistor M2 can be coupled to the gate of transistor M3 by way of operational amplifier OP. For example, the gate of transistor M2 can connect to the non-inverting input terminal of operational amplifier OP, and the inverting input and output terminals of operational amplifier OP can connect to the gate of transistor M3. Thus, operational amplifier OP can not only follow the voltage (e.g., the gate voltage of transistor M3 follows the gate voltage of transistor M2), but may also isolate subsequent circuits from preceding circuits. The current mirror formed by transistors M2 and M3 can replicate the current flowing through transistor M2 to the output terminal, in order to amplify the current.

Figure 4:
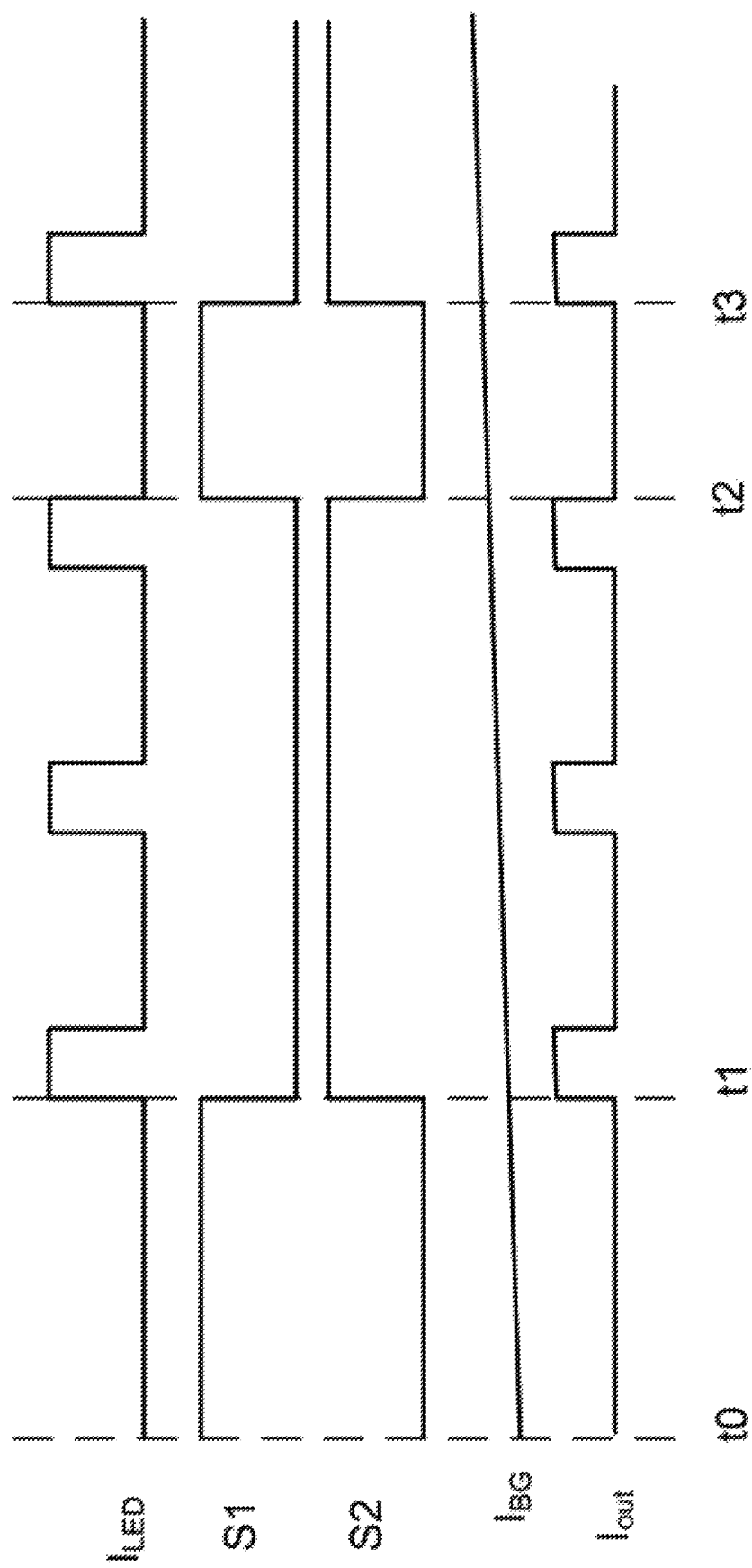
FIG. 4 is a waveform diagram of example operation of an ambient light filter, in accordance with embodiments of the present invention.

Referring now to FIG. 4, shown is a waveform diagram of example operation of an ambient light filter, in accordance with embodiments of the present invention. The photo-electric conversion circuit can receive total current $I_{in}$ from the optical signal, and total current $I_{in}$ may be a sum of current component $I_d$ from the optical pulse signal and current component $I_{BG}$ from the ambient light. Current component $I_d$ can be zero when the light emitting device is not presently emitting light, and current component $I_{BG}$ can dynamically change along with the ambient light. From t0 to t1, light emitting device 11 may not be emitting light. Photo-electric conversion circuit 13 may only be exposed to the ambient light, and control circuit 143 can control switch S1 to turn on, and switch S2 to turn off. Sample and hold circuit A can operate in the first mode, and most of current component $I_{BG}$ caused by the ambient light may flow through one side of sample and hold circuit A, and the current component that flows through one side of current detection circuit B may be negligible, i.e., $I_{in} \approx I_{BG}$, $I_d \approx 0$.

From t1 to t2, light emitting device 11 can begin operating (e.g., emitting light). The photo-electric conversion circuit can be exposed to the optical pulse signal reflected by the object and the ambient light. Thus, control circuit 143 can control switch Si to turn off, and switch S2 to turn on, and sample and hold circuit A may operate in the second mode (e.g., current component $I_{BG}$ remains stable). The current component that corresponds to the ambient light can remain flowing through sample and hold circuit A. Thus, the current component caused by the ambient light can be filtered from input optical signal $I_{in}$, and the current component caused by the optical pulse signal may through current detection circuit B, and can also be provided to the current amplifier. Therefore, effects of the ambient light can be substantially eliminated without increasing the power consumption of the light emitting device.

From t2 to t3, after a predetermined number of pulse emitting periods has elapsed (e.g., 3), in the gap of pulse emitting periods, light emitting device 11 may not be emitting light. The photo-electric conversion circuit may only be exposed to the ambient light. Control circuit 143 can control switch S1 to turn on, and switch S2 to turn off, and sample and hold circuit A may operate in the first mode. Most of current component $I_{BG}$ caused by the ambient light can flow through one side of sample and hold circuit A, and the current component that flows through one side of current detection circuit B may be negligible. It can be seen from the example of FIG. 4 that the photo pulse gap during the time interval from t2 to t3 is in the middle of the entire photo pulse sequence, and the photo pulse sequence of a full measurement may not yet be completed. In this way, the ambient light can be detected for several times in the middle of the measurement, in order to ensure the accuracy of ambient light filter.

From time t3, the circuit can switch to the second mode to repeat the filtering operation, and after a predetermined time interval, the current component that corresponds to the ambient light can be sampled in the photo pulse gap. The photo sensor of particular embodiments can be applied in heart rate detectors, or photo detectors for obtaining an object by detecting the intensity of the light reflected by the object (e.g., a distance detection apparatus, etc.).

In particular embodiments, the sample and detection circuit can be configured to sample the ambient light in a first mode, and filter the ambient light component from the optical current in a second mode. Also, the control circuit that is used to control the modes of the sample and detection circuit can be configured to switch the sample and detection circuit to the first mode in at least one optical pulse gap, and to switch the sample and detection circuit to the second mode when the next optical pulse arrives. Thus, the ambient light can be detected for one or more times during the detection period, in order to improve the accuracy of the photo sensor and the associated photo detector without significantly increasing the power consumption. In this way, good performance may be achieved in a variety of environments.

The embodiments were chosen and described in order to best explain the principles of the invention and its practical applications, to thereby enable others skilled in the art to best utilize the invention and various embodiments with modifications as are suited to particular use(s) contemplated. It is intended that the scope of the invention be defined by the claims appended hereto and their equivalents.

What is claimed is:

1. An ambient light filter configured to filter ambient light noises from an optical current that is at least partially caused by an optical pulse sequence emitted by a light emitting device, the ambient light filter comprising:
  a) a sample and detection circuit configured to sample said optical current and to obtain a current component in a first mode, and to remove said current component from said optical current and to generate a detection signal in a second mode;
  b) a current amplifier configured to receive said detection signal, and to generate an amplified current signal; and
  c) a control circuit configured to switch said sample and detection circuit between said first and second modes, wherein said control circuit switches said sample and detection circuit to said first mode in at least one optical pulse gap, and switches said sample and detection circuit to said second mode when a next optical pulse arrives.

2. The ambient light filter of claim 1, wherein said control circuit switches said sample and detection circuit to said first mode in said optical pulse gap every predetermined number of optical pulse periods.

3. The ambient light filter of claim 1, wherein said sample and detection circuit comprises:
  a) a sample and hold circuit coupled to an optical current input terminal, and being configured to cause said optical current of a first proportion to flow in said first mode, and to maintain an intensity of said optical current in said second mode;
  b) a current detection circuit that forms a current mirror with said sample and hold circuit in said first mode, and being configured to cause said optical current of a second proportion to flow in said first mode, and to allow said optical current shunted by said sample and hold circuit in said second mode, in order to generate a detection signal;
  c) a first switch coupled between said sample and hold circuit and said current detection circuit, and being configured to control modes of said sample and hold circuit; and
  d) said control circuit being configured to control said first switch so as to control said sample and detection circuit to switch between said first and second modes, wherein said first proportion is far greater than said second proportion.

4. The ambient light filter of claim 3, wherein said ambient light filter comprises:
  a) a second switch coupled to said current amplifier, wherein said current amplifier is enabled when said second switch is turned on, and disabled when said second switch is turned off; and
  b) said control circuit being configured to turn off said second switch when said first switch is turned on, and to turn on said second switch when said first switch is turned off.

5. The ambient light filter of claim 3, wherein said sample and hold circuit comprises:
  a) a first transistor coupled between said optical current input terminal and ground;
  b) a low-pass filter coupled between a gate of said first transistor and a mode control terminal; and
  c) a capacitor coupled between said mode control terminal and ground.

6. The ambient light filter of claim 5, wherein said current detection circuit comprises:
  a) a second transistor coupled between said optical current input terminal and ground, wherein a gate of said second transistor is coupled to a source thereof; and
  b) said first switch is coupled between said mode control terminal and said gate of said second transistor, wherein a size of said first transistor is greater than a size of said second transistor.

7. The ambient light filter of claim 3, wherein said sample and hold circuit comprises:
  a) a plurality of parallel coupled first transistors coupled between said optical current input terminal and ground, wherein gates of each of said plurality of said first transistors are coupled together;
  b) a low-pass filter coupled between said gates of said plurality of first transistors and a mode control terminal; and
  c) a capacitor coupled between said mode control terminal and ground.

8. The ambient light filter of claim 7, wherein said current detection circuit comprises:

a) a second transistor coupled between said optical current input terminal and ground, a gate of said second field effect transistor is coupled to a source thereof; and b) said first switch is coupled between said mode control terminal and said gate of said second transistor, wherein a size of said plurality of first transistors is greater than a size of said second transistor.

9. The ambient light filter of claim 8, wherein a size of each of said plurality of first transistors is the same as a size of said second transistor.

10. A photo sensor, comprising the ambient light filter of claim 1, and further comprising:

a) a light emitting device configured to emit light;

b) a driving circuit configured to drive said light emitting device to emit light; and c) a photo-electric conversion circuit coupled to said ambient light filter, and being configured to generate said optical current according to an optical signal.

11. The photo sensor of claim 10, being configured in a heart rate detector.

12. The photo sensor of claim 10, being configured in a distance detection apparatus.

\* \* \* \* \*